US00PP28877P3

(12) United States Plant Patent
Wood

(10) Patent No.: US PP28,877 P3
(45) Date of Patent: Jan. 16, 2018

(54) ***LAGERSTROEMIA* PLANT NAMED 'SMLIPINK102'**

(50) Latin Name: *Lagerstroemia indica*
Varietal Denomination: SMLIPINK102

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 39 days.

(21) Appl. No.: 14/998,758

(22) Filed: Feb. 9, 2016

(65) Prior Publication Data

US 2017/0231138 P1 Aug. 10, 2017

(51) Int. Cl.
*A01H 5/00* (2006.01)

(52) U.S. Cl.
USPC ..... Plt./252

(58) Field of Classification Search
USPC ..... Plt./252
See application file for complete search history.

*Primary Examiner* — Susan McCormick Ewoldt
(74) *Attorney, Agent, or Firm* — Cassandra Bright

(57) ABSTRACT

A new and distinct *Lagerstroemia* cultivar named 'SMLIPINK102' is disclosed, characterized by vibrant pink blooms, appearing early in the season. Plants have a compact stature and are very floriferous. The new variety is a *Lagerstroemia*, normally used for ornamental horticulture purposes.

2 Drawing Sheets

Latin name of the genus and species: *Lagerstroemia indica.*

Variety denomination: 'SMLIPINK102'.

BACKGROUND OF THE INVENTION

The new *Lagerstroemia* cultivar is a product of a planned breeding program conducted by the inventor, Timothy D. Wood, in Grand Haven, Mich. The objective of the breeding program was to produce new *Lagerstroemia* varieties for ornamental commercial applications. The open pollination resulting in this new variety was made during July of 2007.

The seed parent is the, patented commercial variety referred to as *Lagerstroemia* 'Red Filli' U.S. Plant Pat. No. 14,353. The pollen parent is unknown as it was an open pollination breeding program. The new variety was selected July of 2010 by the inventor in a group of seedlings resulting from the 2007 open pollination, in a seedling trial field in Grand Haven, Mich.

Asexual reproduction of the new cultivar was performed by softwood cuttings. This was first performed at Spring Meadow Nursery in Grand Haven, Mich. during July of 2010 and has shown that the unique features of this cultivar are stable and reproduced true to type in 4 successive generations.

SUMMARY OF THE INVENTION

The cultivar 'SMLIPINK102' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMLIPINK102' These characteristics in combination distinguish 'SMLIPINK102' as a new and distinct *Lagerstroemia* cultivar:

1. Vibrant pink blooms.
2. Early flowering.
3. Very floriferous.
4 Compact plant stature.

Plants of the new cultivar 'SMLIPINK102' are similar to plants of the seed parent, *Lagerstroemia* 'Red Filli' in most horticultural characteristics, however, plants of the new cultivar 'SMLIPINK102' differ in the following;

1. Upright/compact habit, whereas the seed parent has an upright and outwardly growing habit
2. Red stem new growth. The comparator has reddish-green new stem growth.

COMMERCIAL COMPARISON

Plants of the new cultivar 'SMLIPINK102' are comparable to the commercial variety *Lagerstroemia* 'G2X133271' U.S. Plant Pat. No. 27,474. The two *Lagerstroemia* varieties are similar in most horticultural characteristics; however, the new variety 'SMLIPINK102' differs in the following:

1. New stem growth more red. The comparator has new stem growth is more brown-red.
2. Earlier flowering. The new variety begins flowering earlier in June than this comparator.

BRIEF DESCRIPTION OF THE PHOTOGRAPHS

Figure 1:
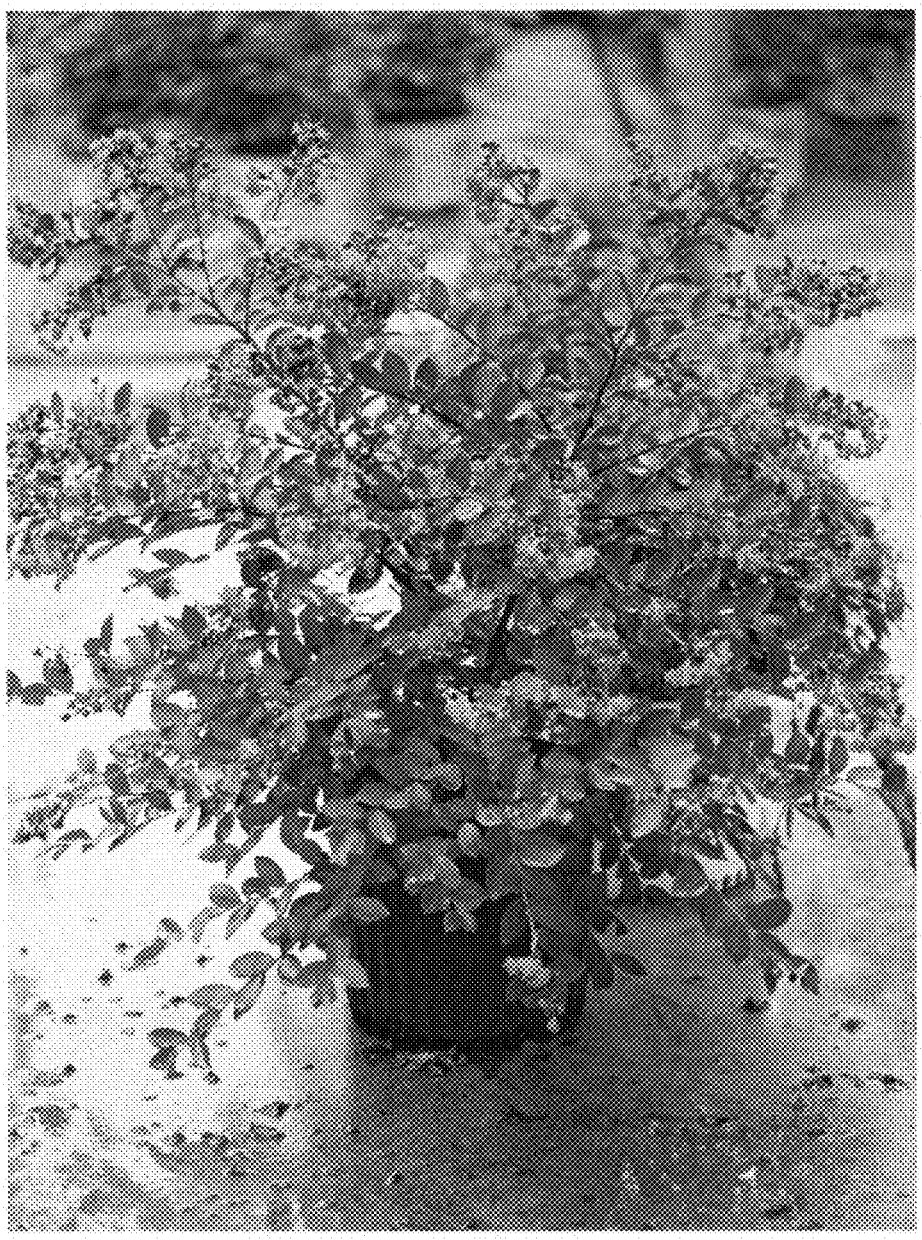

The accompanying photograph in FIG. 1 illustrates in full color a typical plant of 'SMLIPINK102' grown in a greenhouse in Grand Haven Mich. Age of the plant photographed is approximately 2 years old from a rooted cutting.

Figure 2:
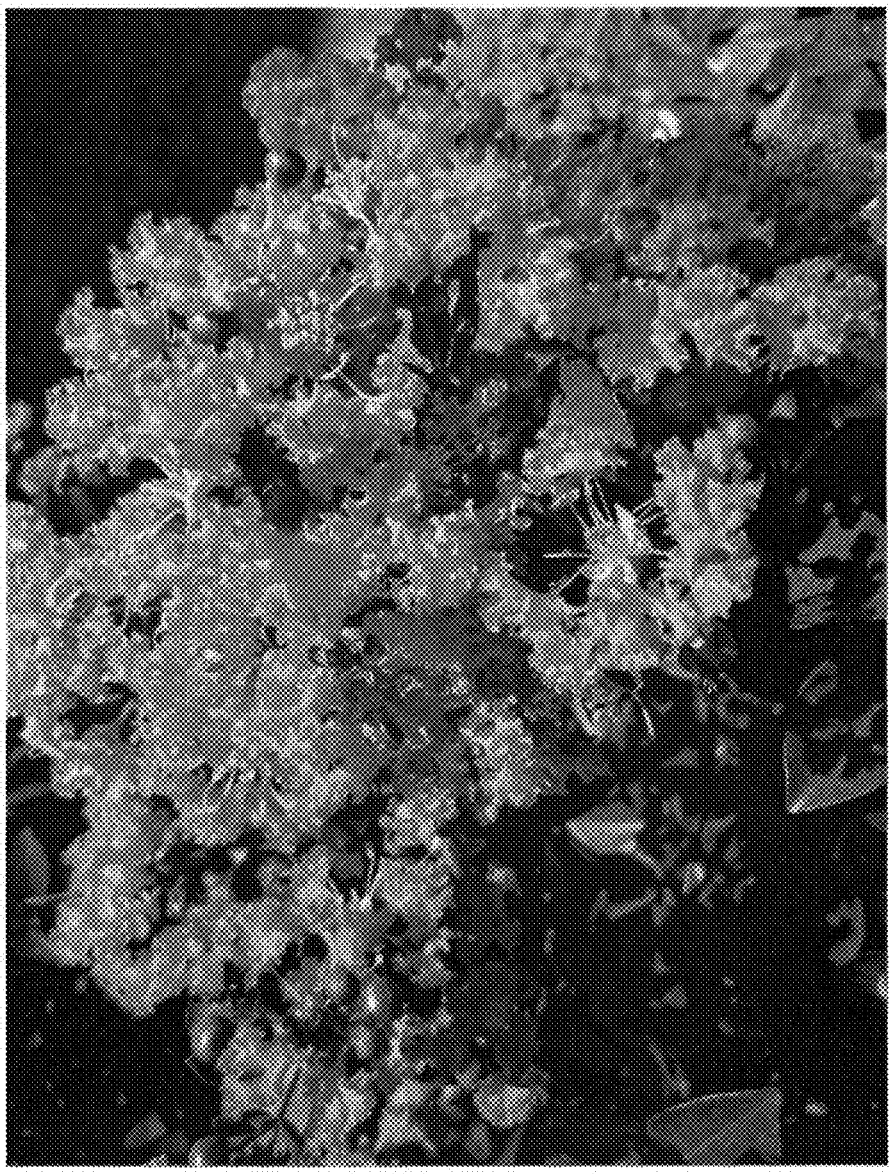

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart sixth 2015 except where general terms of ordinary dictionary significance are used. The following observations and measurements describe 'SMLIPINK102' plants grown in a poly house during Summer of 2015 in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'SMLIPINK102'.

PROPAGATION

Type of propagation typically used: Terminal vegetative cutting.

Time to initiate roots: About 14-21 days 24° C.

Time to produce a rooted cutting: About 35-42 days at 24° C.

Root description: Thin fibrous, not fleshy, freely branching. White in color, not accurately measured with R.H.S. Chart.

PLANT

Age of plant described: 2-3 years old from a rooted cutting.
Container size: 3 gallon container.
Overall plant shape: Upright.
Growth habit: Freely branching outward.
Plant spread: 85 cm.
Plant height: 85 cm.
Growth rate: Strong.
Plant vigor: Good.
Branching habit: Basal, some pinching required.
Length of primary lateral branches: 75 cm.
Diameter of lateral branches: 1.3 cm.
Quantity of lateral branches: 7.
Stem:
- *Color*.—Near RHS Brown 200B blending upward to new growth of Red-purple 60A.
- *Shape*.—Square shaped stem.
- *Strength*.—Strong.
- *Aspect angle*.—5-45°.
- *Texture*.—Pubescent, then woody with age.
- *Other*.—Stem color provides bold contrast to the foliage and flowers.

Internode length: 1.9 cm.

FOLIAGE

Leaf:
- *Arrangement*.—Sub-opposite to alternate, single.
- *Quantity*.—Approximately 18 to 28 per main branch.
- *Average length*.—New growth: 1.6 cm Old Growth: 5.2 cm.
- *Average width*.—New growth: 0.75 cm Old Growth: 2.6 cm.
- *Shape of blade*.—Lance-ovate.
- *Apex*.—Acute.
- *Base*.—Rounded.
- *Margin*.—Entire.
- *Texture of top surface*.—Smooth, waxy.
- *Texture of bottom surface*.—Smooth, waxy.
- *Color*.—Young foliage upper side: Near RHS Greyed-purple 187B blended with Green 137B. Young foliage under side: Near RHS Greyed-purple 187B blended with Green 137C. Mature foliage upper side: Near RHS Green 137A with Greyed-purple 187B on margin and faded tip. Mature foliage under side: Near RHS Yellow-green 146C blended with Greyed-purple 187B.
- *Venation*.—Type: Pinnate. Venation color upper side: Near RHS Greyed-purple 187C. Venation color under side: Near RHS Yellow-green 145B.
- *Petiole*.—Average Length: 2 mm. Diameter: 1 mm. Color: Upper: Near RHS Yellow-green 145B. Lower: Near RHS Yellow-green 145B. Texture upper and lower: Smooth, coriaceous.

FLOWER

Natural flowering season: June through October.
Flower arrangement: Terminal panicles.
Inflorescence form: Panicles.
Flowers per inflorescence: 25-50.
Inflorescence size:
- *Width*.—14.5 cm.
- *Height*.—12 cm.

Individual flowers:
- *Type*.—Rotate.
- *Shape*.—Whorl of 6 freely attached petals.
- *Habit*.—Outward facing.
- *Diameter*.—3.4 cm.
- *Length*.—4 cm.
- *Depth*.—1.5 cm.
- *Persistence*.—Self-cleaning.
- *Fragrance*.—Slight to no scent.

Petals:
- *Arrangement*.—Whorled, not fused.
- *Number*.—6.
- *Shape*.—Orbicular.
- *Margin*.—Irregular undulate.
- *Tip shape*.—Rounded.
- *Base shape*.—Rounded.
- *Length*.—Average 1.4 cm.
- *Width*.—Average 1 cm.
- *Texture*.—Upper: Soft, smooth, delicate papery. Lower: Soft, smooth, delicate papery.
- *Color*.—When opening: Upper surface: Near RHS Red-Purple 61C. Under surface: Near RHS Red-Purple 61C. Fully opened: Upper surface: Near RHS Red-Purple 61C. Under surface: Near RHS Red-Purple 61C. Fading: Upper surface: Near RHS Red-Purple 61C. Under surface: Near RHS Red-Purple 61C.

Bud:
- *Shape*.—Obovate.
- *Length*.—6.5 mm.
- *Diameter*.—7 mm.
- *Color*.—Near RHS Red-purple 60A blended with Greyed-green 196B.

Sepals:
- *Appearance*.—Healthy, variations of color.
- *Arrangement*.—Unguiculate.
- *Shape*.—Narrowly triangular.
- *Tip shape*.—Acute.
- *Base shape*.—Obtuse.
- *Margin*.—Entire.
- *Quantity per flower*.—6.
- *Length*.—5 mm.
- *Width*.—4 mm.

*Margin*.—Entire.
*Texture*.—Upper: Smooth, coriaceous, rugose. Lower: Smooth.
*Color*.—Upper: Near RHS Greyed-purple 184A. Lower: Near RHS Red-purple 59A.

Calyx:
*Shape*.—Unguiculate.
*Length*.—5 mm.
*Diameter*.—6.5 mm.

Peduncle:
*Length*.—1 cm.
*Diameter*.—0.5-1 mm.
*Texture*.—Smooth.
*Color*.—Near RHS Red-purple 60A.
*Orientation*.—Upright and outward.
*Strength*.—Good.

Pedicel:
*Length*.—9 mm.
*Diameter*.—0.5-1 mm.
*Angle*.—5-35°.
*Strength*.—Good.
*Texture*.—Smooth.
*Color*.—Near RHS Red-purple 60A.

REPRODUCTIVE ORGANS

Stamens:
*Number*.—About 32.
*Filament length*.—0.5-1.3 cm.
*Filament color*.—Near RHS Greyed-red 181C blended with White 155B towards base.

Anthers:
*Shape*.—Orbital.
*Length*.—1 mm.
*Color*.—Near RHS Yellow-orange 15B.
*Pollen*.—Color: Near RHS Yellow 12B. Quantity: Good.

Pistil:
*Number*.—1.
*Length*.—2.2 cm.
*Style*.—Length: 1.9 cm. Color: Near RHS Greyed-yellow 160B fades up to Greyed-red 179C.

Stigma:
*Shape*.—Globe.
*Color*.—Near RHS Yellow-green 152B.
*Ovary color*.—Near RHS Yellow 10C.

OTHER CHARACTERISTICS

Disease/pest resistance: Neither resistance nor susceptibility to normal diseases of *Lagerstroemia*.

Garden performance: Good tolerance of environmental stressors, noted to perform well in harsh winters.

What is claimed is:

1. A new and distinct cultivar of *Lagerstroemia* plant named 'SMLIPINK102' as herein illustrated and described.

* * * * *